United States Patent [19]

Hamaguchi et al.

[11] Patent Number: 5,140,041
[45] Date of Patent: Aug. 18, 1992

[54] 1-PHENOXYCARBONYL-2-PYRROLIDI-NONE DERIVATIVES AND NOOTROPIC AGENTS

[75] Inventors: Fumiko Hamaguchi, Tokyo; Tatsuo Nagasaka, Hachioji; Einosuke Sakurai, Ohimachi, all of Japan

[73] Assignee: Nisshin Flour Milling Co., Ltd., Tokyo, Japan

[21] Appl. No.: 658,300

[22] Filed: Feb. 20, 1991

[30] Foreign Application Priority Data

Feb. 20, 1990 [JP] Japan .................................. 2-39064

[51] Int. Cl.$^5$ ...................... A61K 31/40; C07D 207/12
[52] U.S. Cl. ...................... 514/423; 548/531
[58] Field of Search ......................... 548/531; 514/423

[56] References Cited

U.S. PATENT DOCUMENTS 4,369,139  1/1983  Kyburz et al. ..................... 548/539

FOREIGN PATENT DOCUMENTS 0003602  8/1979  European Pat. Off. .
0044088  1/1982  European Pat. Off. .
0304330  2/1989  European Pat. Off. .
0373226  6/1990  European Pat. Off. .

*Primary Examiner*—Joseph Paul Brust
*Attorney, Agent, or Firm*—Oblon, Spivak, McClelland, Maier & Neustadt

[57] ABSTRACT

1-Phenoxycarbonyl-2-pyrrolidinone derivatives of formula (I) or (I') are disclosed.

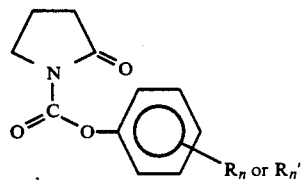

wherein R is a $C_1$–$C_6$ alkyl group, a $C_1$–$C_6$ alkoxy group, a nitro group or a halogen atom and n is 1 or 2, and R' is the same as R, but including further a hydrogen atom. The compounds of formula (I') are useful as nootropic agents.

10 Claims, No Drawings

1-PHENOXYCARBONYL-2-PYRROLIDINONE DERIVATIVES AND NOOTROPIC AGENTS

FIELD OF THE INVENTION

This invention relates to new 1-phenoxycarbonyl-2-pyrrolidinone derivatives, processes for preparing the same and nootropic agents comprising said derivatives as an active ingredient.

BACKGROUND OF THE INVENTION

Pyrrolidinone derivatives have heretofore been known as drugs for cerebral insufficiency disease and so on. For instance, U.S. Pat. No. 4,369,139 discloses that 1-(p-methoxybenzoyl)-2-pyrrolidinone is useful in the prevention of cerebral insufficiency. European Patent 0 304 330 A1 discloses that 1-phenoxycarbonyl-2-pyrrolidinone is an intermediate for the preparation of carbamoylpyrrolidone derivatives which are useful as drugs for senile dementia, or as psychotropic and/or antiamnesia agents. However, said European patent gives no reference to the use as nootropic agents of 1-phenoxycarbonyl-2-pyrrolidinone and its derivatives having substituted phenyl.

DISCLOSURE OF THE INVENTION

The present invention provides new compounds of formula (I)

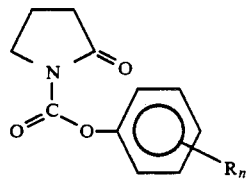

(I)

wherein R is a $C_1-C_6$ alkyl group, a $C_1-C_6$ alkoxy group, a nitro group or a halogen atom and n is 1 or 2.

The present inventors have found that the compounds of formula (I') including further hydrogen in the definition of R for formula (I) are useful as nootropic agents capable of using in the inhibition or prevention of cerebral insufficiency, improvement or therapy of amnesia, improvement, inhibition or therapy of senile dementia and improvement of intellectual capacity in such conditions as cerebral seizure and alcoholism. Thus, the present invention also provides nootropic agents comprising the compounds of formula (I') as an active ingredient.

The terms used in the definition of formula (I) and formula (I') are further illustrated below. The definition of R' in the claims is the same as R, but including further hydrogen. Representative of $C_1-C_6$ alkyl group includes methyl, ethyl, n-propyl, iso-propyl, n-butyl, sec-butyl, iso-butyl, tert-butyl, n-amyl and n-hexyl.

Representative of $C_1-C_6$ alkoxy group includes methoxy, ethoxy, n-propoxy, iso-propoxy, n-butoxy, iso-butoxy, tert-butoxy, amyloxy and hexyloxy. Representative of halogen atom includes fluorine, chlorine and bromine.

Representative compounds of the present invention are exemplified below.

1-(2'-methoxyphenoxycarbonyl)-2-pyrrolidinone;
1-(3'-methoxyphenoxycarbonyl)-2-pyrrolidinone;
1-(4'-methoxyphenoxycarbonyl)-2-pyrrolidinone;
1-(2'-methylphenoxycarbonyl)-2-pyrrolidinone;
1-(3'-methylphenoxycarbonyl)-2-pyrrolidinone;
1-(4'-methylphenoxycarbonyl)-2-pyrrolidinone;
1-(4'-fluorophenoxycarbonyl)-2-pyrrolidinone;
1-(2'-chlorophenoxycarbonyl)-2-pyrrolidinone;
1-(3'-chlorophenoxycarbonyl)-2-pyrrolidinone;
1-(4'-chlorophenoxycarbonyl)-2-pyrrolidinone;
1-(2'-bromophenoxycarbonyl)-2-pyrrolidinone;
1-(3'-bromophenoxycarbonyl)-2-pyrrolidinone;
1-(4'-bromophenoxycarbonyl)-2-pyrrolidinone;
1-(2',6'-dibromophenoxycarbonyl)-2-pyrrolidinone;
1-(2'-nitrophenoxycarbonyl)-2-pyrrolidinone;
1-(3'-nitrophenoxycarbonyl)-2-pyrrolidinone;
1-(4'-nitrophenoxycarbonyl)-2-pyrrolidinone;
1-(2',6'-dimethoxyphenoxycarbonyl)-2-pyrrolidinone; and
1-(3',5'-dimethoxyphenoxycarbonyl)-2-pyrrolidinone.

The compounds of the invention can be prepared by reacting phenol or substituted phenol with phosgen to form corresponding chloroformylated phenol or substituted phenol followed by reacting with 2-pyrrolidinone or a reactive derivative of 2-pyrrolidinone, for example, 1-trimethylsilyl-2-pyrrolidinone. The reactions are represented by the following reaction scheme.

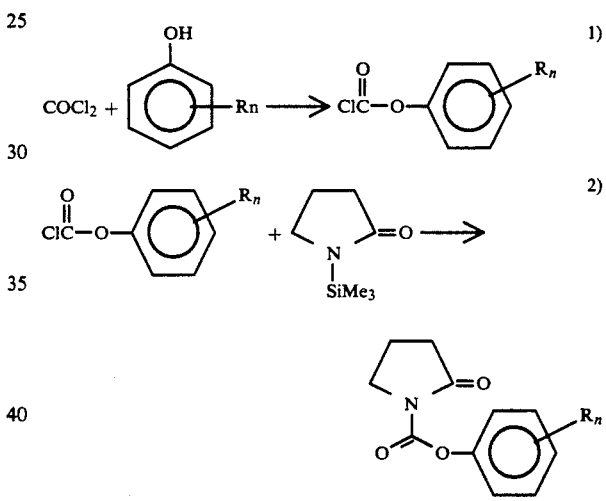

In the above formulas, R and n are as defined above.

In the first step 1) the reaction is carried out by reacting phenol or substituted phenol with phosgen in approximately equimolar amounts in an organic solvent, e.g., an aromatic hydrocarbon solvent in the presence of an acid binder such as an inorganic or organic base in a conventional manner for chloroformylation.

In the second step 2), the reaction is effected by reacting the chloroformylated product formed in the first step, with or without isolation, with 2-pyrrolidinone in the presence of an acid binder, e.g., an inorganic or organic base, or by reacting said chloroformylated product with 1-trimethylsilyl-2-pyrrolidinone. The amounts of the chloroformylated product and 2-pyrrolidinone or trimethylsilyl pyrrolidinone may be substantially equimolar amount.

The crude products of the invention as produced after distilling off the solvent are purified by known means such as recrystallization, chromatography or the like.

As previously mentioned, the compounds of formula (I') can be used for inhibition or prevention of cerebral insufficiency, improvement or therapy of amnesia, improvement, inhibition or therapy of senile dementia and improvement of intellectual capacity in such conditions as cerebral seizure and alcoholism.

The compounds of formula (I') can be formulated in various dosage forms. The pharmaceutical preparations can be administered orally in the form of tablets, sugar-coated tablets, hard capsules, soft capsules, or liquids such as solutions, emulsions or suspensions. Alternatively, the preparations may be administered rectally in the form of suppositories or parenterally in the form of injections.

These pharmaceutical preparations can be produced by known processes using additives well known in the art such as excipients, binders, dilluents, stabilizers, preservatives, solubilizers, wetting agents, emulsifiers, lubricants, sweetners, colorants, flavoring agents, buffers and antioxidants. Dosage of the present compounds is variable in a wide range, generally a daily dose of about 5 to 2500 mg/kg.

The invention is further illustrated by the following non-limitative examples.

EXAMPLE 1

1-Phenoxycarbonyl-2-pyrrolidinone

To a solution of phenyl chloroformate (3.13 g, 20.0 mmol) in anhydrous toluene (10 ml) was added a solution of 1-trimethylsilyl-2-pyrrolidinone (3.46 g, 22.0 mmol) in anhydrous toluene (10 ml). The mixture was stirred at room temperature for 30 min. The reaction mixture was evaporated under reduced pressure to dryness to give a solid material. Recrystallization from ethanol afforded 2.37 g of colorless prisms. Yield 57.7%.

m.p.: 123°–124° C.

IR(KBr):3006, 2969, 2841, 1796, 1698, 1506, 1380, 1308, 1192, 994 cm$^{-1}$ $^1$H-NMR(400 MHz, CDCl$_3$)δ:7.38(2H, t, J=7.5 Hz, H-3',5'), 7.24(1H, t, J=7.5 Hz, H-4'), 7.18(2H, d, J=7.5 Hz, H-2',6'), 3.95(2H, t, J=8.1 Hz, H-5), 2.61(2H, t, J=7.6 Hz, H-3), 2.12(2H, quintet, J=7.8 Hz, H-4)

Mass spectrum m/e): 205(M+), 112

Elementary analysis: (for C$_{11}$H$_{11}$NO$_3$)

|         | C %   | H %  | N %  |
|---------|-------|------|------|
| Calc'd: | 64.38 | 5.40 | 6.85 |
| Found:  | 64.42 | 5.43 | 6.78 |

EXAMPLE 2

1-(2'-Methoxyphenoxycarbonyl)-2-pyrrolidinone

To a solution of phosgen (6.27 g, 63.3 mmol) in anhydrous benzene (30 ml) was dropwise added under ice-cooling a solution of 2-methoxyphenol (7.86 g, 63.3 mmol) and purified pyridine (5.00 g, 63.3 mmol) in anhydrous benzene (20 ml). The mixture was stirred overnight at room temperature. From a reaction solution were separated white precipitates by filtration, and a filtrate was evaporated under reduced pressure to give a colorless oily material. The oily material was dissolved in anhydrous benzene (20 ml), to which was added a solution of 1-trimethylsilyl-2-pyrrolidinone (9.66 g, 63.3 mmol) in anhydrous benzene (10 ml). The mixture was stirred at room temperature for 30 min. The reaction mixture was evaporated under reduced pressure to dryness to give a solid material. The desired product was separated using column chromatography on silica gel (eluted with benzene-acetone 20:1→1:1). Recrystallization from 2-propanol afforded colorless prisms. Yield 29.4% m.p.: 104°–105° C.

IR(KBr):3071, 3050, 3031, 1790, 1701, 1611, 1589, 1300, 762, 746 cm$^{-1}$ $^1$H-NMR(400 MHz, CDCl$_3$)δ:7.21(1H, t, J=7.9 Hz, H-5'), 7.11(1H, dd, J=7.9, 1.5 Hz, H-6'), 7.95(1H, t, J=7.9 Hz, H-4'), 6.92(1H, dd, J=7.9, 1.0 Hz, H-3'), 3.95 (2H, t, J=8.1 Hz, H-5), 3.81 (3H, s, 2'-OCH$_3$), 2.59 (2H, t, J=7.6 Hz, H-3), 2.09 (2H, quintet, J=7.8 Hz, H-4)

Mass spectrum (m/e): 235(M+), 124

Elementary analysis: (for C$_{12}$H$_{13}$NO$_4$)

|         | C %   | H %  | N %  |
|---------|-------|------|------|
| Calc'd: | 61.27 | 5.57 | 5.96 |
| Found:  | 61.32 | 5.62 | 5.97 |

EXAMPLE 3

1-(4'-Methoxyphenoxycarbonyl)-2-pyrrolidinone

To a solution of 4-methoxyphenyl chloroformate (3.73 g, 20.2 mmol) in anhydrous toluene (10 ml) was added a solution of 1-trimethylsilyl-2-pyrrolidinone (3.46 g, 22.0 mmol) in anhydrous toluene (10 ml). The mixture was stirred at room temperature for 30 min. The reaction mixture was evaporated under reduced pressure to dryness to give a solid material. Recrystallization from ethanol afforded 3.45 g of colorless prisms. Yield 73.4% m.p.: 133°–134° C.

IR(KBr):3006, 2969, 1799, 1698, 1506, 1380, 1309, 1192, 1170, 994, 746 cm$^{-1}$ $^1$H-NMR(400 MHz, CDCl$_3$),δ:7.10 (2H, d, J=9.1 Hz, H-2',6'), 6.89(2H, d, J=9.1 Hz, H-3',5'), 3.93(2H, t, J=7.2 Hz, H-5), 3.80(3H, s, 4'-OCH$_3$), 2.60(2H, t, J=8.2 Hz, H-3), 2.11(2H, quintet, J=7.6 Hz, H-4)

Mass spectrum (m/e): 235(M+), 124

Elementary analysis: (for C$_{12}$H$_{13}$NO$_4$)

|         | C %   | H %  | N %  |
|---------|-------|------|------|
| Calc'd: | 61.27 | 5.57 | 5.96 |
| Found:  | 61.22 | 5.91 | 5.62 |

EXAMPLE 4

1-(3'-Methoxyphenoxycarbonyl)-2-pyrrolidinone

To a solution of phosgen (6.38 g, 64.5 mmol) in anhydrous benzene (30 ml) was added under ice-cooling a solution of 3-methoxyphenol (4.00 g, 32.3 mmol) and purified pyridine (2.55 g, 32.3 mmol) in anhydrous benzene (20 ml), and the same procedures as in Example 2 were repeated to obtain the product. Recrystallization from 2-propanol gave 2.44 g of colorless prisms. Yield 32.2% m.p.: 45°–47° C.

IR(KBr):3066, 2977, 1800, 1709, 1306, 1138, 767, 692 cm$^{-1}$ $^1$H-NMR(400 MHz, CDCl$_3$)δ:7.26(1H, t, J=8.2 Hz, H-5'), 6.77(3H, m, H-2',4',6'), 3.92(2H, t, J=7.2 Hz, H-5), 3.78(3H, s, 3'-OCH$_3$), 2.59(2H, t, J=8.1 Hz, H-3), 2.09(2H, quintet, J=7.8 Hz, H-4)

Mass spectrum (m/e): 235(M+), 124

EXAMPLE 5

1-(2'-Methylphenoxycarbonyl)-2-pyrrolidinone

To a solution of phosgen (6.00 g, 60.6 mmol) in anhydrous benzene (30 ml) was added under ice-cooling a solution of 2-methylphenol (o-cresol, 6.55 g, 60.6 mmol) and purified pyridine (4.79 g, 60.6 mmol) in anhydrous benzene (20 ml), and the same procedures as in Example 2 were repeated to obtain the product. Recrystallization from 2-propanol gave 7.16 g of colorless prisms. Yield 54.5% m.p.: 85°–87° C.

IR(KBr):3385, 2910, 1796, 1689, 1614, 1585, 1493, 1463, 760 cm$^{-1}$ $^1$H-NMR(400 MHz, CDCl$_3$)δ:7.18(4H, m, H-3',4',5',6'), 3.95(2H, t, J=8.1 Hz, H-5), 2.63(2H, t, J=7.6 Hz, H-3), 2.25(3H, s, 2'-CH$_3$), 2.13(2H, quintet, J=7.8 Hz, H-4)

Mass spectrum (m/e): 219(M+), 108

Elementary analysis: (for C$_{12}$H$_{13}$NO$_3$)

|  | C % | H % | N % |
| --- | --- | --- | --- |
| Calc'd: | 65.74 | 5.98 | 6.39 |
| Found: | 65.81 | 6.39 | 6.39 |

EXAMPLE 6

1-(3'-Methylphenoxycarbonyl)-2-pyrrolidinone

To a solution of phosgen (6.55 g, 65.8 mmol) in anhydrous benzene (30 ml) was added under ice-cooling a solution of 3-methylphenol (m-cresol, 7.12 g, 65.8 mmol) and purified pyridine (5.20 g, 65.8 mmol) in anhydrous benzene (20 ml), and the same procedures as in Example 2 were repeated to obtain the product. Recrystallization from 2-propanol gave 5.75 g of colorless prisms. Yield 39.9% m.p.: 58°–59° C.

IR(KBr):3394, 3052, 1795, 1703, 1614, 1586, 1510, 1488, 783 cm$^{-1}$ $^1$H-NMR(400 MHz, CDCl$_3$)δ:7.25(1H, t, J=7.7 Hz, H-5'), 7.05(1H, d, J=7.7 Hz, H-4'), 7.00(1H, s, H-2'), 6.98(1H, d, J=7.7 Hz, H-6'), 3.93(2H, t, J=7.2 Hz, H-5), 2.60(2H, t, J=8.1 Hz, H-3), 2.35(3H, s, 3'-CH$_3$), 2.09(2H, quintet, J=7.8 Hz, H-4)

Mass spectrum (m/e): 219(M+), 108

Elementary analysis: (for C$_{12}$H$_{13}$NO$_3$)

|  | C % | H % | N % |
| --- | --- | --- | --- |
| Calc'd: | 65.74 | 5.98 | 6.39 |
| Found: | 65.94 | 6.09 | 6.39 |

EXAMPLE 7

1-(4'-Methylphenoxycarbonyl)-2-pyrrolidinone

To a solution of phosgen (5.61 g, 56.6 mmol) in anydrous benzene (30 ml) was added under ice-cooling a solution of 4-methylphenol (p-cresol, 6.17 g, 56.6 mmol) and purified pyridine (4.47 g, 56.6 mmol) in anydrous benzene (20 ml), and the same procedures as in Example 2 were repeated to obtain the product. Recrystallization from 2-propanol gave 1.94 g of colorless prisms. Yield 15.7% m.p.: 101°–102° C.

IR(KBr):3071, 3031, 1785, 1695, 1509, 1464, 824 cm$^{-1}$ $^1$H-NMR(400 MHz, CDCl$_3$)δ:7.17(2H, d, J=8.4 Hz, H-3',5'), 7.06(2H, d, J=8.4 Hz, H-2',6'), 3.94(2H, t, J=7.2 Hz, H-5), 2.61(2H, t, J=8.1 Hz, H-3), 2.34(3H, s, 4'-CH$_3$), 2.11(2H, quintet, J=7.6 Hz, H-4)

Mass spectrum (m/e): 219(M+), 108

Elementary analysis: (for C$_{12}$H$_{13}$NO$_3$)

|  | C % | H % | N % |
| --- | --- | --- | --- |
| Calc'd: | 65.74 | 5.98 | 6.39 |
| Found: | 65.74 | 6.05 | 6.33 |

EXAMPLE 8

1-(4'-Fluorophenoxycarbonyl)-2-pyrrolidinone

To a solution of 4-fluorophenyl chloroformate (3.55 g, 20.0 mmol) in anhydrous benzene (10 ml) was added a solution of 1-trimethylsilyl-2-pyrrolidinone (3.46 g, 22.0 mmol) in anhydrous benzene (10 ml). The mixture was stirred at room temperature for 30 min. The reaction mixture was evaporated under reduced pressure to dryness to give a solid material. Recrystallization from 2-propanol afforded 2.24 g of colorless prisms. Yield 46.9% m.p.: 89°–90° C.

IR(KBr):3385, 2913, 1789, 1698, 1505, 1299, 1167, 875 cm$^{-1}$ $^1$H-NMR(400 MHz, CDCl$_3$)δ:7.14(2H, dd, J=9.0, 4.0 Hz, H-2',6'), 7.06(2H, dd, J=8.8, 8.6 Hz, H-3',5'), 3.94(2H, t, J=7.2 Hz, H-5), 2.61(2H, t, J=7.6 Hz, H-3), 2.09(2H, quintet, J=7.8 Hz, H-4)

Mass spectrum (m/e): 239(M+), 112(M+-FC$_6$H$_4$O)

Elementary analysis: (for C$_{11}$H$_{10}$NO$_3$F)

|  | C % | H % | N % |
| --- | --- | --- | --- |
| Calc'd: | 59.18 | 4.52 | 6.28 |
| Found: | 59.13 | 4.58 | 6.24 |

EXAMPLE 9

1-(2'-Chlorophenoxycarbonyl)-2-pyrrolidinone

To a solution of phosgen (6.04 g, 61.0 mmol) in anhydrous benzene (30 ml) was added under ice-cooling a solution of 2-chlorophenol (7.84 g, 61.0 mmol) and purified pyridine (4.82 g, 61.0 mmol) in anhydrous benzene (20 ml), and the same procedures as in Example 2 were repeated to obtain the product. Recrystallization from 2-propanol gave 4.23 g of colorless prisms. Yield 28.9% m.p.: 92°–93° C.

IR(KBr):3098, 1807, 1700, 1487, 1463, 1371, 1308, 1220, 762 cm$^{-1}$ $^1$H-NMR(400 MHz, CDCl$_3$)δ:7.90(1H, d, J=7.9 Hz, H-3'), 7.25(3H, m, H-4',5',6'), 4.00(2H, t, J=7.1 Hz, H-5), 2.63(2H, t, J=8.0 Hz, H-3), 2.13(2H, quintet, J=7.8 Hz, H-4)

Mass spectrum (m/e): 239(M+), 112(M+-ClC$_6$H$_4$O)

Elementary analysis: (for C$_{11}$H$_{10}$NO$_3$Cl)

|  | C % | H % | N % |
| --- | --- | --- | --- |
| Calc'd: | 55.12 | 4.21 | 5.85 |
| Found: | 55.22 | 4.24 | 5.88 |

EXAMPLE 10

1-(3'-Chlorophenoxycarbonyl)-2-pyrrolidinone

To a solution of phosgen (5.79 g, 58.5 mmol) in anhydrous benzene (30 ml) was added under ice-cooling a solution of 3-chlorophenol (7.52 g, 58.5 mmol) and purified pyridine (4.62 g, 58.8 mmol) in anhydrous benzene (20 ml) and the same procedures as in Example 2 were repeated to obtain the product. Recrystallization from 2-propanol gave 4.24 g of colorless prisms. Yield 30.2% m.p.: 88°–89° C.

IR(KBr):3397, 3087, 1796, 1703, 1596, 1587, 1477, 1459, 1304, 995, 757, 679 cm$^{-1}$ $^1$H-NMR(400 MHz, CDCl$_3$)$\delta$:7.31(1H, t, J=8.1 Hz, H-5'), 7.23(2H, m, H-2',4'), 7.10(1H, d, J=7.2 Hz, H-6'), 3.93(2H, t, J=6.9 Hz, H-5), 2.61(2H, t, J=8.1 Hz, H-3), 2.11(2H, quintet, J=7.5 Hz, H-4)

Mass spectrum (m/e): 239(M$^+$), 112(M$^+$-ClC$_6$H$_4$O)

Elementary analysis: (for C$_{11}$H$_{10}$NO$_3$Cl)

|         | C %   | H %  | N %  |
| ------- | ----- | ---- | ---- |
| Calc'd: | 55.12 | 4.21 | 5.85 |
| Found:  | 55.14 | 4.27 | 5.83 |

EXAMPLE 11

1-(4'-Chlorophenoxycarbonyl)-2-pyrrolidinone

To a solution of phosgen (5.94 g, 60.0 mmol) in anhydrous benzene (30 ml) was added under ice-cooling a solution of 4-chlorophenol (7.71 g, 60.0 mmol) and purified pyridine (4.74 g, 60.0 mmol) in anhydrous benzene (20 ml), and the same procedures as in Example 2 were repeated to obtain the product. Recrystallization from 2-propanol gave 5.55 g of colorless prisms. Yield 42.1% m.p.: 99°–100° C.

IR(KBr):3094, 3040, 1786, 1703, 1490, 1304, 756 cm$^{-1}$ $^1$H-NMR(400 MHz, CDCl$_3$)$\delta$:7.33(2H, d, J=8.5 Hz, H-3',5'), 7.12(2H, d, J=8.5 Hz, H-2',6'), 3.91(2H, t, J=7.2 Hz, H-5), 2.59(2H, t, J=8.0 Hz, H-3), 2.11(2H, quintet, J=7.6 Hz, H-4)

Mass spectrum (m/e): 239(M$^+$), 112(M$^+$-ClC$_6$H$_4$O)

Elementary analysis: (for C$_{11}$H$_{10}$NO$_3$Cl)

|         | C %   | H %  | N %  |
| ------- | ----- | ---- | ---- |
| Calc'd: | 55.12 | 4.21 | 5.85 |
| Found:  | 55.14 | 4.28 | 5.84 |

EXAMPLE 12

1-(2'-Bromophenoxycarbonyl)-2-pyrrolidinone

To a solution of phosgen (6.10 g, 61.6 mmol) in anhydrous benzene (30 ml) was added under ice-cooling a solution of 1-bromophenol (10.66 g, 61.6 mmol) and purified pyridine (4.87 g, 61.6 mmol) in anhydrous benzene (20 ml), and the same procedures as in Example 2 were repeated to obtain the product. Recrystallization from 2-propanol gave 4.93 g of colorless prisms. Yield 28.2% m.p.: 103°–104° C.

IR(KBr):3449, 2909, 1806, 1702, 1473, 1372, 1308, 989, 762 cm$^{-1}$ $^1$H-NMR(400 MHz, CDCl$_3$)$\delta$:7.61(1H, dd J=8.0, 1.5 Hz, H-3'), 7.34(1H, td, J=8.0, 8.0, 1.5 Hz, H-5'), 7.26(1H, dd, J=8.0, 1.6 Hz, H-6'), 7.14(1H, td, J=8.0, 8.0, 1.6 Hz, H-4'), 4.03(2H, t, J=7.1 Hz, H-5), 2.64(2H, t, J=8.0 Hz, H-3), 2.15(2H, quintet, J=7.7 Hz, H-4)

Mass spectrum (m/e): 283(M$^+$), 112(M$^+$-BrC$_6$H$_4$O)

Elementary analysis: (for C$_{11}$H$_{10}$NO$_3$Br)

|         | C %   | H %  | N %  |
| ------- | ----- | ---- | ---- |
| Calc'd: | 46.49 | 3.55 | 4.93 |
| Found:  | 46.59 | 3.63 | 4.95 |

EXAMPLE 13

1-(3'-Bromophenoxycarbonyl)-2-pyrrolidinone

To a solution of phosgen (3.67 g, 37.1 mmol) in anhydrous benzene (30 ml) was added under ice-cooling a solution of 3-bromophenol (6.42 g, 37.1 mmol) and purified pyridine (2.93 g, 37.1 mmol) in anhydrous benzene (20 ml), and the same procedures as in Example 2 were repeated to obtain the product. Recrystallization from 2-propanol gave 3.68 g of colorless prisms. Yield 35.0% m.p.: 95°–96° C.

IR(KBr):3388, 3082, 2976, 1796, 1702, 1589, 1301, 1190, 995, 756, 678 cm$^{-1}$ $^1$H-NMR(400 MHz, CDCl$_3$)$\delta$:7.38(2H, m, H-2',4'), 7.26(1H, t, J=8.3 Hz, H-5'), 7.15(1H, d, J=8.3 Hz, H-6'), 3.93(2H, t, J=7.0 Hz, H-5), 2.61(2H, t, J=8.1 Hz, H-3), 2.12(2H, quintet, J=7.5 Hz, H-4)

Mass spectrum (m/e): 283(M$^+$), 112(M$^+$-BrC$_6$H$_4$O)

Elementary analysis: (for C$_{11}$H$_{10}$NO$_3$Br)

|         | C %   | H %  | N %  |
| ------- | ----- | ---- | ---- |
| Calc'd: | 46.49 | 3.55 | 4.93 |
| Found:  | 46.58 | 3.61 | 4.97 |

EXAMPLE 14

1-(4'-Bromophenoxycarbonyl)-2-pyrrolidinone

To a solution of 4-bromophenyl chloroformate (4.19 g, 20.0 mmol) in anhydrous benzene (20 ml) was added a solution of 1-trimethylsilyl-2-pyrrolidinone (3.46 g, 22.0 mmol) in anhydrous benzene (10 ml). The mixture was stirred at room temperature for 30 min. The reaction mixture was evaporated under reduced pressure to dryness to give a solid material. Recrystallization from 2-propanol afforded 3.00 g of colorless prisms. Yield 53% m.p.: 107°–108° C.

IR(KBr):3387, 3088, 1800, 1780, 1699, 1582, 1483, 1305, 1192, 991, 757 cm$^{-1}$ $^1$H-NMR(400 MHz, CDCl$_3$)$\delta$:7.49(2H, d, J=8.8 Hz, H-3',5'), 7.07(2H, d, J=8.8 Hz, H-2',6'), 3.93(2H, t, J=7.2 Hz, H-5), 2.62(2H, t, J=8.0 Hz, H-3), 2.12(2H, quintet, J=7.6 Hz, H-4)

Mass spectrum (m/e): 283(M$^+$), 112(M$^{30}$-BrC$_6$H$_4$O)

Elementary analysis: (for C$_{11}$H$_{10}$NO$_3$Br)

|         | C %   | H %  | N %  |
| ------- | ----- | ---- | ---- |
| Calc'd: | 46.49 | 3.55 | 4.93 |
| Found:  | 46.42 | 3.62 | 4.95 |

EXAMPLE 15

1-(2'-Nitrophenoxycarbonyl)-2-pyrrolidinone

To a solution of phosgen (6.12 g, 61.8 mmol) in anhydrous benzene (30 ml) was dropwise added under ice-cooling a solution of 2-nitrophenol (8.60 g, 61.8 mmol) and purified pyridine (4.88 g, 61.8 mmol) in anhydrous benzene (20 ml). The mixture was stirred for 30 min. at room temperature. From the reaction solution were separated precipitates by filtration, and a filtrate was evaporated under reduced pressure to give a colorless oily material. The oily material was dissolved in anhydrous benzene (20 ml), to which was added a solution of 1-trimethylsilyl-2-pyrrolidinone (4.00 g, 25.4 mmol) in anhydrous benzene (10 ml). The mixture was stirred at room temperature for 30 min. The reaction mixture was evaporated under reduced pressure to dryness to give a solid material. The desired product was separated using column chromatography on silica gel (eluted with chloroform-acetone 30:1→3:1). Recrystallization from ethanol afforded 1.98 g of colorless prisms. Yield 31.1% m.p.: 135°–136° C.

IR(KBr):3400, 3109, 2992, 1805, 1703, 1606, 1590, 1371, 1247, 1310, 1217, 1188, 989, 738 cm$^{-1}$ $^1$H-NMR(400 MHz, CDCl$_3$)δ:8.14(1H, d, J=8.1 Hz, H-3'), 7.68(1H, t, J=8.1 Hz, H-5'), 7.44(1H, t, J=8.1 Hz, H-4'), 7.36 (1H, d, J=8.1 Hz, H-6'), 3.99(2H, t, J=7.2 Hz, H-5), 2.64(2H, t, J=8.0 Hz, H-3), 2.16(2H, quintet, J=7.8 Hz, H-4)

Mass spectrum (m/e): 250(M+), 112(M+-NO$_2$C$_6$H$_4$O)

Elementary analysis: (for C$_{11}$H$_{10}$N$_2$O$_5$)

|  | C % | H % | N % |
|---|---|---|---|
| Calc'd: | 52.80 | 4.03 | 11.20 |
| Found: | 52.77 | 4.13 | 11.25 |

EXAMPLE 16

1-(3'-Nitrophenoxycarbonyl)-2-pyrrolidinone

To a solution of phosgen (5.89 g, 59.5 mmol) in anhydrous benzene (30 ml) was added under ice-cooling a solution of 3-nitrophenol (8.28 g, 59.5 mmol) and purified pyridine (4.70 g, 59.5 mmol) in anhydrous benzene (20 ml), and the same procedures as in Example 15 were repeated to obtain the product. Recrystallization from ethanol gave 4.41 g of pale yellow prisms. Yield 58.8% m.p.: 130°–131° C.

IR(KBr):3393, 3102, 2998, 1795, 1703, 1531, 1352, 1304, 1273, 1211, 1191, 1160, 995, 816, 736 cm$^{-1}$ $^1$H-NMR(400 MHz, CDCl$_3$)δ:8.12(2H, m, H-4',5'), 7.77(2H, m, H-2',6'), 3.97(2H, t, J=6.9 Hz, H-5), 2.63(2H, t, J=8.1 Hz, H-3), 2.16(2H, quintet, J=7.5 Hz, H-4)

Mass spectrum (m/e): 250(M+), 112(M+-NO$_2$C$_6$H$_4$O)

EXAMPLE 17

1-(4'-Nitrophenoxycarbonyl)-2-pyrrolidinone

To a solution of phosgen (6.35 g, 64.2 mmol) in anhydrous benzene (30 ml) was added under ice-cooling a solution of 4-nitrophenol (10.10 g, 64.2 mmol) and purified pyridine (5.07 g, 64.2 mmol) in anhydrous benzene (20 ml), and the same procedures as in Example 15 were repeated to obtain the product. Recrystallization from ethanol gave 2.86 g of colorless prisms. Yield 35.6% m.p.: 122°–123° C.

IR(KBr):3396, 3078, 2998, 1807, 1784, 1704, 1612, 1595, 1515, 1312, 1230, 994, 861, 757 cm$^{-1}$ $^1$H-NMR(400 MHz, CDCl$_3$)δ:8.28(2H, d, J=9.2 Hz, H-3',5'), 7.39(2H, d, J=9.2 Hz, H-2',6'), 3.96(2H, t, J=7.2 Hz, H-5), 2.64(2H, t, J=8.0 Hz, H-3), 2.16(2H, quintet, J=7.6 Hz, H-4)

Mass spectrum (m/e): 250(M+), 112(M+-NO$_2$C$_6$H$_4$O)

Elementary analysis: (for C$_{11}$H$_{10}$N$_2$O$_5$)

|  | C % | H % | N % |
|---|---|---|---|
| Calc'd: | 52.80 | 4.03 | 11.20 |
| Found | 52.75 | 4.08 | 11.27 |

EXAMPLE 18

1-(2',6'-Dimethoxyphenoxycarbonyl)-2-pyrrolidinone

To a solution of phosgen (5.80 g, 58.6 mmol) in anhydrous benzene (30 ml) was added under ice-cooling a solution of 2,6-dimethoxyphenol (9.03 g, 58.6 mmol) and purified pyridine (4.63 g, 58.6 mmol) in anhydrous benzene (20 ml), and the same procedures as in Example 2 were repeated to obtain the product. Recrystallization from ethanol gave 5.35 g of colorless prisms. Yield 34.5% m.p.: 163°–165° C.

IR(KBr):2894, 2740, 1790, 1699, 1619, 1483, 1312, 1113, 761 cm$^{-1}$ $^1$H-NMR (400 MHz, CDCl$_3$)δ:7.13(1H, t, J=8.4 Hz, H-4'), 6.66(2H, d, J=8.4 Hz, H-3',5'), 3.87(2H, t, J=7.1 Hz, H-5), 3.75(6H, s, 2',6'-OCH$_3$), 2.58(2H, t, J=8.0 Hz, H-3), 2.09(2H, quintet, J=7.8 Hz, H-4)

Mass spectrum (m/e): 265(M+), 154

Elementary analysis: (for C$_{13}$H$_{15}$NO$_5$)

|  | C % | H % | N % |
|---|---|---|---|
| Calc'd: | 58.86 | 5.70 | 5.28 |
| Found: | 58.76 | 5.76 | 5.15 |

EXAMPLE 19

1-(3',5'-Dimethoxyphenoxycarbonyl)-2-pyrrolidinone

To a solution of phosgen (6.16 g, 62.2 mmol) in anhydrous benzene (30 ml) was added under ice-cooling a solution of 3,5-dimethoxyphenol (9.59 g, 62.2 mmol) and purified pyridine (4.63 g, 62.2 mmol) in anhydrous benzene (20 ml), and the same procedures as in Example 2 were repeated to obtain the product. Recrystallization from 2propanol gave 5.13 g of pale brown prisms. Yield 31.1% m.p.: 80°–81° C.

IR(KBr):2968, 1790, 1775, 1626, 1592, 1468, 1329, 1312, 1158, 993, 868, 769 cm$^{-1}$ $^1$H-NMR(90 MHz, CDCl$_3$)δ:6.35(3H, s, H-2',4',6'), 3.90(2H, t, J=7.0 Hz, H-5), 3.75(6H, s, 3',5'-OCH$_3$), 2.60(2H, t, J=8.0 Hz, H-3), 2.10(2H, quintet, J=7.0 Hz, H-4)

Mass spectrum (m/e): 265(M+), 154

Representative compounds of the invention were evaluated for an activity against amnesia using "passive avoidance" test with a scopolamine-induced amnesia.

Passive Avoidance

The test apparatus was a light chamber (10×14×20 cm) and a dark chamber (24×24×20 cm) with a stainless grid floor to which an electroshock can be applied by a shock generator (SGS-002, manufactured by Muromachi Machine Co., Ltd.). The passive avoidance test was conducted on 3 groups of 10 DDY mice (male, 5 weeks age). To the animals of the first group as a control, CMC was orally administered and after 30 minutes, a solution of scopolamine in physiological saline was subcutaneously administered at a dose of 1.0 mg/kg. To other two groups, the test compounds, i.e., 1-(p-methoxybenzoyl)-2-pyrrolidinone (aniracetam) as a comparative compound and the present compounds were orally administered at doses of 30 mg/kg and after 30 minutes, a solution of scopolamine in physiological saline was subcutaneously administered at a dose of 1.0 mg/kg. 30 minutes after the subcutaneous administration, the acquisition trial was conducted and 24 hours thereafter the retention trial was conducted.

Acquisition Trial

Mice were individually placed in the light chamber at a direction opposite to the passage inlet. A latency at which the limb of a mouse completely enters the dark chamber was measured. A foot shock (1 mA, for 0.5 sec.) was delivered through the grid floor as soon as the mouse entered the dark chamber. Thereafter, each mouse was returned to a conventional case.

Retention Trial 24 hours after the acquisition trial, each mouse was again placed in the light chamber in accordance with the same procedure as done in the previous day. The latency was measured. In this case, no foot shock was given.

In the following table, the results are shown as percent change in latencies over control defined as 100.

| Effects of Compounds against Amnesia | |
|---|---|
| Test Compound | Anti-amnesic activity (%) |
| Aniracetam | 161.3 |
| Compound of Example 5 | 280.2 |
| Compound of Example 7 | 242.4 |
| Compound of Example 10 | 270.0 |
| Compound of Example 12 | 604.5 |
| Compound of Example 15 | 542.2 |
| Compound of Example 17 | 288.3 |

In view of the pharmacological activity the compounds of formula (I') can be used in various dosage forms depending upon the object of administration. Particular formulations are illustrated below.

Formulation Example 1—Tablets (one tablet)

| 1-(2'-Bromophenoxycarbonyl)-2-pyrrolidinone (Active ingredient) | 10 mg |
|---|---|
| Lactose | 67 mg |
| Crystalline cellulose | 15 mg |
| Corn starch | 7 mg |
| Magnesium stearate | 1 mg |
| | 100 mg |

The components were uniformly blended to prepare powders for direct compression. The powders were formulated by a rotary tableting machine into tablets each 6 mm in diameter and weighing 100 mg.

Formulation Example 2—Granules (one divided form)

| 1-(2'-Bromophenoxycarbonyl)-2-pyrrolidinone (Active ingredient) | 10 mg |
|---|---|
| Lactose | 90 mg |
| Corn starch | 50 mg |
| Crystalline cellulose | 50 mg |
| Hydroxypropylcellulose | 10 mg |
| Ethanol | 90 mg |

The active ingredient, lactose, corn starch and crystalline cellulose were uniformly blended, to which were added a solution of hydroxypropylcellulose and ethanol. The mixture was kneaded and granulated by extrusion granulation. The granules were dried in a drier at 50° C. and screened to particle sizes of 297 μm–1460 μm. The granular formulation was divided into 200 mg per division.

Formulation Example 3—Syrup

| 1-(2'-Bromophenoxycarbonyl)-2-pyrrolidinone (Active ingredient) | 1.000 g |
|---|---|
| Sucrose | 30.000 g |
| D-Sorbitol 70 w/v % | 25.000 g |
| Ethyl paraoxybenzoate | 0.030 g |
| Propyl paraoxybenzoate | 0.015 g |
| Flavors | 0.200 g |
| Glycerin | 0.150 g |
| 96% Ethanol | 0.500 g |
| Distilled water | q.s. |
| Total | 100 ml |

Sucrose, D-sorbitol, methyl paraoxybenzoate, propyl paraoxybenzoate and the active ingredient were dissolved in 60 g of warm water. To the solution, after cooling, were added glycerin and the flavors dissolved in the ethanol. To the mixture was then added water to make up 100 ml.

Formulation Example 4—Injections

| 1-(2'-Bromophenoxycarbonyl)-2-pyrrolidinone (Active ingredient) | 2 mg |
|---|---|
| CMC | 2 mg |
| Distilled water | 1 mg |

CMC and the active ingredient were suspended in distilled water to prepare an injection.

Formulation Example 5—Suppositories

| 1-(2'-Bromophenoxycarbonyl)-2-pyrrolidinone (Active ingredient) | 2 g |
|---|---|
| Polyethylene glycol 4000 | 20 g |
| Glycerin | 78 g |
| Total | 100 g |

The active ingredient was dissolved in glycerin. To the solution was added polyethylene glycol 4000, and the mixture was warmed to a solution. The solution was poured into a suppository mold and solidified by cooling to prepare suppositories weighing 1.5 g per piece.

What is claimed is:

1. A compound of Formula (I)

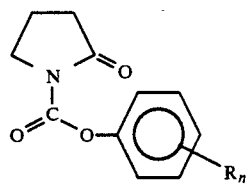 (I)

wherein R is a $C_1$-$C_6$ alkyl group, a $C_1$-$C_6$ alkoxy group, a nitro group or a halogen atom.

2. The compound of claim 1, wherein R is a $C_1$-$C_4$ alkyl group.

3. The compound of claim 1, wherein R is a $C_1$-$C_4$ alkoxy group.

4. The compound of claim 1, wherein R is a nitro group.

5. The compound of claim 1, wherein R is F, Cl or Br.

6. A nootropic agent comprising as an active ingredient an effective amount of a compound of Formula (I)

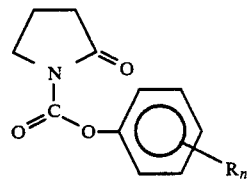 (I)

wherein R is a $C_1$-$C_6$ alkyl group, a $C_1$-$C_6$ group, a nitro group or a halogen atom and a pharmaceutically acceptable carrier.

7. The nootropic agent of claim 6, wherein R is a $C_1$-$C_4$ alkyl group.

8. The nootropic agent of claim 6, wherein R is a $C_1$-$C_4$ alkoxy group.

9. The nootropic agent of claim 6, wherein R is a nitro group.

10. The nootropic agent of claim 6, wherein R is F, Cl or Br.

* * * * *

UNITED STATES PATENT AND TRADEMARK OFFICE
CERTIFICATE OF CORRECTION

PATENT NO. : 5,140,041

DATED : AUGUST 18, 1992

INVENTOR(S) : FUMIKO HAMAGUCHI ET AL

It is certified that error appears in the above-identified patent and that said Letters Patent is hereby corrected as shown below:

Columns 13 and 14, Formula (I):

Delete the subscript "n" from "$R_n$" (i.e. amend "$R_n$" to read --R--).

Column 14, Claim 6

Amend "$C_1$-$C_6$ group" to read --$C_1$-$C_6$ <u>alkoxy</u> group--.

Signed and Sealed this

Thirty-first Day of August, 1993

*Attest:*

BRUCE LEHMAN

*Attesting Officer*   *Commissioner of Patents and Trademarks*